(12) United States Patent
Dexter et al.

(10) Patent No.: US 10,314,610 B2
(45) Date of Patent: Jun. 11, 2019

(54) SLANTED DRIVE AXIS ROTARY SURGICAL CUTTING TOOLS AND POWERED HANDPIECES

(71) Applicant: MEDTRONIC PS MEDICAL, INC., Minneapolis, MN (US)

(72) Inventors: S. Shane Dexter, Keller, TX (US); Zachary Heiliger, Flower Mound, TX (US)

(73) Assignee: Medtronic PS Medical, Inc., Minneapolis, MN (US)

( * ) Notice: Subject to any disclaimer, the term of this patent is extended or adjusted under 35 U.S.C. 154(b) by 469 days.

(21) Appl. No.: 15/072,492

(22) Filed: Mar. 17, 2016

(65) Prior Publication Data

US 2016/0278788 A1 Sep. 29, 2016

Related U.S. Application Data

(60) Provisional application No. 62/138,334, filed on Mar. 25, 2015.

(51) Int. Cl.
*A61B 17/16* (2006.01)
*A61B 17/3205* (2006.01)

(52) U.S. Cl.
CPC ........ *A61B 17/3205* (2013.01); *A61B 17/162* (2013.01)

(58) Field of Classification Search
CPC ............ A61B 17/1616; A61B 17/1617; A61B 17/1624; A61B 17/1631;
(Continued)

(56) References Cited

U.S. PATENT DOCUMENTS

| 233,709 A | 10/1880 | Starr |
|---|---|---|
| 288,676 A | 11/1883 | Stearns |

(Continued)

FOREIGN PATENT DOCUMENTS

| CH | 686 113 | 1/1996 |
|---|---|---|
| DE | 88 15 261.8 | 3/1989 |

(Continued)

OTHER PUBLICATIONS

Product Catalog—vol. 9, Brasseler USA, CASE 0:11-cv-01404-MJD-FLN Document 40-3 Filed Nov. 18, 2011—7 pgs.
International Search Report and Written Opinion for International Application No. PCT/US2016/018686 dated Jul. 22, 2016 (17 pgs).

*Primary Examiner* — Matthew J Lawson
(74) *Attorney, Agent, or Firm* — Dicke, Billig & Czaja, PLLC

(57) ABSTRACT

A surgical cutting tool adapted to be rotatably driven by a motor. The surgical cutting tool includes an elongated shaft defining intermediate and coupling portions. A shape of the intermediate portion defines a primary central axis of the shaft. The coupling portion includes a tang having a tapered cylindrical shape that defines a drive axis. The drive axis is slanted with respect to the primary central axis. When coupled to the motor of a powered handpiece, the tang transmits an input or drive force from the motor to the intermediate portion as a torque about the primary central axis. In some embodiments, the drive axis extends through a centroid of first and second spaced apart cross-sectional planes of the tang, the first and second planes each being perpendicular to the primary central axis.

19 Claims, 14 Drawing Sheets

(58) Field of Classification Search
CPC .... B23B 2231/0216; B23B 2231/0244; B23B 2231/0288; B23B 2231/0296
USPC ........................................................ 408/226
See application file for complete search history.

(56) References Cited

U.S. PATENT DOCUMENTS

| | | | |
|---|---|---|---|
| 1,043,098 A | 11/1912 | Gross | |
| 1,053,709 A | 2/1913 | Collins | |
| 1,112,349 A | 9/1914 | Barnes | |
| 1,209,362 A | 12/1916 | Turner | |
| 1,539,439 A | 5/1925 | Smith | |
| 1,862,337 A | 6/1932 | Emrick | |
| 2,477,058 A * | 7/1949 | Harborne | B23B 31/008 279/16 |
| 2,512,033 A | 6/1950 | Metz | |
| 2,522,388 A | 9/1950 | Madsen | |
| 2,596,594 A | 5/1952 | Petre | |
| 2,682,184 A | 6/1954 | Szarkowski | |
| 2,726,872 A | 12/1955 | Onsrud | |
| 2,773,693 A | 12/1956 | Chittenden | |
| 3,043,634 A | 7/1962 | Coley | |
| 3,136,347 A | 6/1964 | Linguist | |
| 3,589,826 A | 6/1971 | Fenn | |
| 3,637,225 A | 1/1972 | Schmuck | |
| 3,835,858 A | 9/1974 | Hagen | |
| 4,035,100 A | 7/1977 | Kruger et al. | |
| 4,047,722 A | 9/1977 | Nielsen et al. | |
| 4,078,593 A | 3/1978 | Benitz | |
| 4,107,949 A | 8/1978 | Wanner et al. | |
| 4,123,074 A | 10/1978 | Wanner | |
| 4,146,240 A | 3/1979 | Nielsen | |
| 4,185,383 A | 1/1980 | Heimke et al. | |
| 4,378,053 A | 3/1983 | Simpson | |
| 4,502,734 A | 3/1985 | Allen | |
| 4,512,692 A | 4/1985 | Nielsen et al. | |
| 4,565,472 A | 1/1986 | Brennsteiner et al. | |
| 4,594,036 A | 6/1986 | Hogenhout | |
| 4,655,651 A | 4/1987 | Hunger et al. | |
| 4,823,468 A | 4/1989 | Kollegger | |
| 4,830,000 A | 5/1989 | Shutt | |
| 4,917,274 A | 4/1990 | Asa et al. | |
| 5,009,440 A | 4/1991 | Manschitz | |
| 5,116,353 A | 5/1992 | Green | |
| 5,203,654 A | 4/1993 | Henderson | |
| 5,256,147 A | 10/1993 | Vidal et al. | |
| 5,263,786 A | 11/1993 | Kageyama | |
| 5,286,145 A | 2/1994 | Kleine | |
| 5,352,234 A | 10/1994 | Scott | |
| 5,382,249 A | 1/1995 | Fletcher | |
| 5,421,682 A | 6/1995 | Obermeier et al. | |
| 5,439,005 A | 8/1995 | Vaughn | |
| 5,487,626 A | 1/1996 | Von Holst et al. | |
| 5,499,985 A | 3/1996 | Hein et al. | |
| 5,505,737 A | 4/1996 | Gosselin et al. | |
| 5,549,634 A | 8/1996 | Scott et al. | |
| 5,569,256 A | 10/1996 | Vaughn et al. | |
| D377,982 S | 2/1997 | Walen | |
| 5,601,560 A | 2/1997 | Del Rio et al. | |
| 5,634,933 A * | 6/1997 | McCombs | A61B 17/162 408/226 |
| 5,697,158 A | 12/1997 | Klinzing et al. | |
| 5,720,749 A | 2/1998 | Rupp | |
| 5,735,535 A | 4/1998 | McCombs et al. | |
| 5,741,263 A | 4/1998 | Umber et al. | |
| 5,782,836 A | 7/1998 | Umber et al. | |
| 5,810,802 A | 9/1998 | Panescu et al. | |
| 5,833,704 A | 11/1998 | McCombs et al. | |
| 5,893,851 A | 4/1999 | Umber et al. | |
| 5,928,241 A | 7/1999 | Menut et al. | |
| 5,941,891 A | 8/1999 | Walen | |
| 5,989,257 A | 11/1999 | Tidwell et al. | |
| 6,007,541 A | 11/1999 | Scott | |
| 6,000,940 A | 12/1999 | Buss et al. | |
| 6,062,575 A | 5/2000 | Mickel et al. | |
| 6,209,886 B1 | 4/2001 | Estes et al. | |
| 6,261,035 B1 | 7/2001 | Moores et al. | |
| 6,267,763 B1 | 7/2001 | Castro | |
| 6,290,525 B1 | 9/2001 | Jacobi | |
| 6,409,221 B1 | 6/2002 | Robinson et al. | |
| 6,447,484 B1 | 9/2002 | Briscoe et al. | |
| 6,607,533 B2 | 8/2003 | Del Rio et al. | |
| 6,612,588 B2 | 9/2003 | Ostermeier et al. | |
| 6,688,610 B2 | 2/2004 | Huggins et al. | |
| 6,723,101 B2 | 4/2004 | Fletcher et al. | |
| 6,733,218 B2 | 5/2004 | Del Rio et al. | |
| D492,412 S | 6/2004 | Desoutter et al. | |
| 6,746,153 B2 | 6/2004 | Del Rio et al. | |
| 6,780,189 B2 | 8/2004 | Tidwell et al. | |
| 6,811,190 B1 | 11/2004 | Ray et al. | |
| 6,976,815 B2 * | 12/2005 | Berglow | B23C 5/10 407/54 |
| 7,001,391 B2 | 2/2006 | Estes et al. | |
| 7,011,661 B2 | 3/2006 | Riedel et al. | |
| 7,066,940 B2 | 6/2006 | Riedel et al. | |
| D536,791 S | 2/2007 | Eskridge et al. | |
| 7,261,169 B2 | 8/2007 | Kleine et al. | |
| 7,374,375 B2 | 5/2008 | Kleine et al. | |
| 7,429,154 B2 | 9/2008 | Kleine et al. | |
| 7,465,309 B2 | 12/2008 | Walen | |
| 7,488,327 B2 | 2/2009 | Rathbun et al. | |
| 7,497,860 B2 | 3/2009 | Carusillo et al. | |
| 7,549,992 B2 | 6/2009 | Shores et al. | |
| 7,559,927 B2 | 7/2009 | Shores et al. | |
| D609,810 S | 2/2010 | Cote et al. | |
| 7,669,308 B2 | 3/2010 | Oshnock et al. | |
| 7,691,106 B2 | 4/2010 | Schenberger et al. | |
| 7,722,054 B2 | 5/2010 | Young | |
| D617,900 S | 6/2010 | Kingsley et al. | |
| D617,901 S | 6/2010 | Unger et al. | |
| D617,902 S | 6/2010 | Twomey et al. | |
| D617,903 S | 6/2010 | Unger et al. | |
| 7,766,585 B2 | 8/2010 | Vasudeva et al. | |
| D631,962 S | 2/2011 | Dorman | |
| D636,082 S | 4/2011 | Cote et al. | |
| 7,922,720 B2 | 4/2011 | May et al. | |
| D641,468 S | 7/2011 | Ruiz et al. | |
| 8,043,292 B2 | 10/2011 | Carusillo | |
| D648,021 S | 11/2011 | Dorman | |
| D666,294 S | 8/2012 | Miles et al. | |
| 8,361,068 B2 | 1/2013 | McClurken | |
| 8,419,760 B2 | 4/2013 | Wiebe, III | |
| 8,518,065 B2 | 8/2013 | Shores et al. | |
| D692,134 S | 10/2013 | Lee-Sepsick | |
| 8,597,316 B2 | 12/2013 | McCombs | |
| 8,702,710 B2 | 4/2014 | Carusillo | |
| 8,801,713 B2 | 8/2014 | Del Rio et al. | |
| 8,893,820 B2 | 11/2014 | Barhitte et al. | |
| D728,098 S | 4/2015 | Schad et al. | |
| D728,099 S | 4/2015 | Schad et al. | |
| D744,650 S | 12/2015 | Catron et al. | |
| D746,457 S | 12/2015 | Swick et al. | |
| D747,477 S | 1/2016 | Freigang et al. | |
| D753,826 S | 4/2016 | Eggeling et al. | |
| 2002/0105149 A1 | 8/2002 | Karst | |
| 2002/0151902 A1 | 10/2002 | Riedel et al. | |
| 2002/0171208 A1 | 11/2002 | Lechot et al. | |
| 2003/0097133 A1 | 5/2003 | Green et al. | |
| 2003/0140743 A1 | 7/2003 | Ofentavsek | |
| 2003/0163134 A1 | 8/2003 | Riedel et al. | |
| 2003/0229351 A1 | 11/2003 | Tidwell et al. | |
| 2005/0027282 A1 | 2/2005 | Schweikert et al. | |
| 2005/0072007 A1 | 4/2005 | Proulx | |
| 2005/0232715 A1 | 10/2005 | Baumann et al. | |
| 2006/0053974 A1 | 3/2006 | Blust et al. | |
| 2007/0172321 A1 | 7/2007 | Nagai | |
| 2007/0282329 A1 | 12/2007 | Kawano | |
| 2008/0033280 A1 | 2/2008 | Lubock et al. | |
| 2009/0024129 A1 | 1/2009 | Gordon et al. | |
| 2009/0312779 A1 | 12/2009 | Boykin et al. | |
| 2010/0063524 A1 | 3/2010 | McCombs | |
| 2010/0076477 A1 | 3/2010 | Jezierski et al. | |
| 2011/0022069 A1 | 1/2011 | Mitusina | |
| 2011/0190803 A1 | 8/2011 | To et al. | |

(56) References Cited

U.S. PATENT DOCUMENTS

| | | |
|---|---|---|
| 2011/0218562 A1 | 9/2011 | Viola et al. |
| 2011/0238070 A1 | 9/2011 | Santangelo et al. |
| 2011/0270293 A1 | 11/2011 | Malla et al. |
| 2011/0270294 A1 | 11/2011 | Rubin |
| 2012/0070220 A1 | 3/2012 | Ruiz et al. |
| 2013/0110147 A1 | 5/2013 | Dame |
| 2013/0116659 A1 | 5/2013 | Porter |
| 2013/0138096 A1 | 5/2013 | Benn |
| 2013/0144267 A1 | 6/2013 | Chan et al. |
| 2013/0296848 A1 | 11/2013 | Allen, IV et al. |
| 2014/0056656 A1 | 2/2014 | Bae et al. |
| 2014/0124231 A1 | 5/2014 | Hessenberger et al. |
| 2014/0163558 A1 | 6/2014 | Cosgrove et al. |
| 2014/0336654 A1 | 11/2014 | Pilgeram |
| 2014/0350561 A1 | 11/2014 | Dacosta et al. |
| 2014/0371752 A1 | 12/2014 | Anderson |

FOREIGN PATENT DOCUMENTS

| | | |
|---|---|---|
| DE | 102012101259 | 8/2013 |
| EP | 0293327 | 11/1988 |
| EP | 0216354 | 7/1991 |
| EP | 1101459 | 2/2006 |
| EP | 1289714 | 8/2008 |
| EP | 1514034 | 10/2011 |
| FR | 1330849 | 6/1963 |
| GB | 2129730 | 5/1984 |
| RU | 2077275 | 4/1997 |
| WO | 9608343 | 3/1996 |
| WO | 2001/66024 | 9/2001 |
| WO | 2001/89769 | 11/2001 |
| WO | 2014/037134 | 3/2014 |
| WO | 2014/176060 | 10/2014 |

* cited by examiner

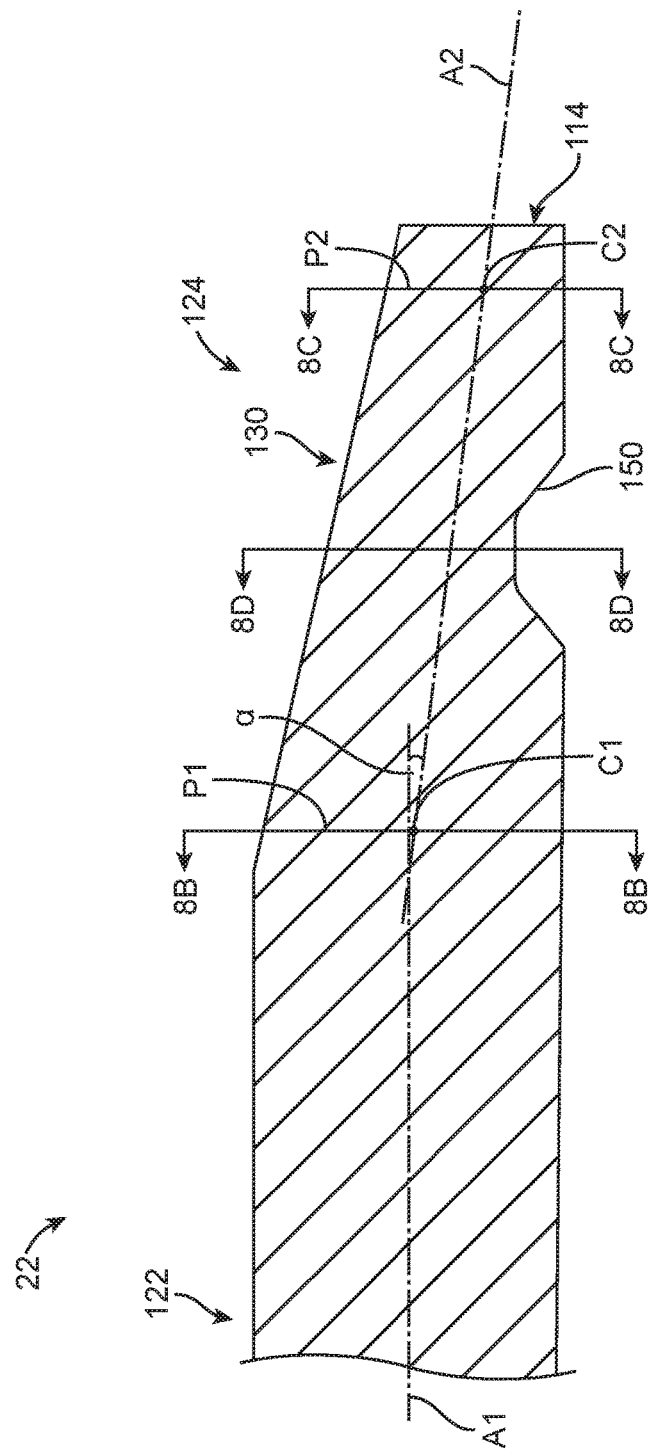

SLANTED DRIVE AXIS ROTARY SURGICAL CUTTING TOOLS AND POWERED HANDPIECES

CROSS REFERENCE TO RELATED APPLICATIONS

This Non-Provisional Patent Application claims the benefit of the filing date of U.S. Provisional Patent Application Ser. No. 62/138,334, filed Mar. 25, 2015, entitled "SKEWED DRIVE AXIS ROTARY SURGICAL CUTTING TOOLS AND POWERED HANDPIECES," which is herein incorporated by reference.

BACKGROUND

The present disclosure relates to rotary-type surgical cutting tools and powered handpieces. More particularly, it relates to rotary surgical cutting tools providing robust driven connection with a powered handpiece.

Powered surgical handpieces are commonly used in many medical specialties to drive surgical tools. For example, powered surgical handpieces are used to drive surgical drills, blades or other cutting tools in performing various diverse cutting-type functions including drilling, tapping, resection, dissection, debridement, shaving, pulverizing, and shaping of anatomical tissue including bone. The handpieces are typically configured for selective coupling to, and driving of, a variety of different rotary-type surgical cutting instruments that are each designed to perform a specific procedure. During use, based upon the specific surgical procedure, the surgeon selects the appropriate surgical tool and mounts it to the powered handpiece. The powered handpiece is then operated to move (e.g., rotation, oscillation) the tool in performing the surgical procedure. Additional procedural steps can later be performed by mounting a differently-styled tool to the same powered handpiece.

The improved capabilities of powered surgical handpieces, as well as the vast number of surgical cutting tools now available, have undoubtedly greatly increased the number of neurological, spine, ENT/head/neck and other procedures that a surgeon can perform utilizing a single surgical system (i.e., a single powered handpiece with multiple surgical cutting tools). Selective driven coupling between the powered handpiece and each tool is typically effectuated within a housing of the handpiece. The housing carries an internal drive chuck configured to receive a tang or shank of the surgical cutting tool in a mating fashion. Thus, the tang of each surgical cutting tool useful with a particular handpiece has a common shape, with this shape corresponding to the handpiece drive chuck (e.g., circular, hexagonal). The drive chuck is connected to (or formed as part of) a drive shaft; upon coupling of the surgical cutting tool to the drive chuck, powered rotation of the drive shaft rotates the cutting tool.

Conventionally, the cutting tool, including the tang, is generally shaped as an elongated cylinder defining a single central axis about which the tool is driven and rotated during use. The handpiece drive chuck forms a corresponding, generally cylindrical-shaped passage for receiving the tang, effectuating a coupled connection and subsequent driven interface at point contacts created solely about the single central axis. The tang (or other regions of the cutting tool) may include recesses, grooves, or other features deviating from a truly cylindrical shape for purposes of effectuating an axial and/or rotational lock relative to the drive chuck. However, an entirety of the conventional tang/drive chuck interface design is premised upon a purely torsional transmission of force directly from the drive chuck to the tang (i.e., solely about the single central axis), and from the tang to a remainder of the cutting tool including the cutting implement. While this approach is widely accepted and well-received, certain drawbacks may arise. Complex machining/grinding is required to achieve the requisite torque transmission and axial retention features, resulting in high contact stresses and reduced interface stiffness. Further, backlash can be prevalent. These potential concerns, in turn, may lead to reliability issues, such as premature tool and/or handpiece failure. Moreover, formation of intricate engagement features along the tang (e.g., hexagonal surface) represents an added cost to what is otherwise sometimes viewed as a single use, disposable product.

In light of the above, a need exists for rotary-type surgical cutting tools and corresponding powered handpieces with reduced operational stresses.

SUMMARY

Some aspects of the present disclosure relate to a surgical cutting tool for use in the dissection of bone, biomaterials and/or other tissue when mated with a motor. The surgical cutting tool includes an elongated shaft defining opposing first and second ends, a dissection portion adjacent the first end, a coupling portion adjacent the second end, and an intermediate portion between the dissection and coupling portions. A shape of the intermediate portion defines a primary central axis of the shaft and about which the shaft rotates during use. The coupling portion includes a tang having a tapered cylindrical shape that defines a drive (or secondary) axis. The drive axis is slanted with respect to the primary central axis; for example, the axes define an oblique angle. With this construction, and when coupled to the motor of a powered surgical handpiece, the slanted axis tang effectively serves as a crank shaft, transmitting an input or drive force from the motor to the intermediate portion as a torque about the primary central axis. In some embodiments, the drive axis extends through a centroid of first and second spaced apart cross-sectional planes of the tang, the first and second planes each being perpendicular to the primary central axis. In yet other embodiments, a perimeter of the tang is continuously curved in a plane perpendicular to the primary central axis. In yet other embodiments, the tapered cylindrical shape is a non-symmetrical tapered cylinder. In yet other embodiments, the coupling portion defines an axial retention feature.

Other aspects of the present disclosure relate to a surgical system for cutting tissue. The system includes a powered handpiece and a surgical cutting tool. The powered handpiece includes a housing, a drive shaft and a drive chuck. The drive shaft is rotatably maintained by the housing, and is rotationally driven by a motor. The drive chuck is connected to the drive shaft. The surgical cutting tool is releasably connectable to the powered handpiece, and includes an elongated shaft defining opposing first and second ends, a dissection portion adjacent the first end, a coupling portion adjacent the second end, and an intermediate portion between the dissection and coupling portions. A shape of the intermediate portion defines a primary central axis of the shaft and about which the shaft rotates during use. The coupling portion includes a tang having a tapered cylindrical shape that defines a drive (or secondary) axis. The drive central axis is slanted with respect to the primary central axis; for example, the axes define an oblique angle. The system is configured such that upon insertion of the tang into the drive chuck and rotation of the drive chuck, a drive force applied to the tang is transmitted as a torque to the intermediate portion about the primary central axis. In some embodiments, rotation of the drive chuck generates a shear force at the tang.

BRIEF DESCRIPTION OF THE DRAWINGS

FIG. 8A is an enlarged longitudinal cross-sectional view of a portion of the surgical cutting tool of FIG. 7;

DETAILED DESCRIPTION

Figure 1:
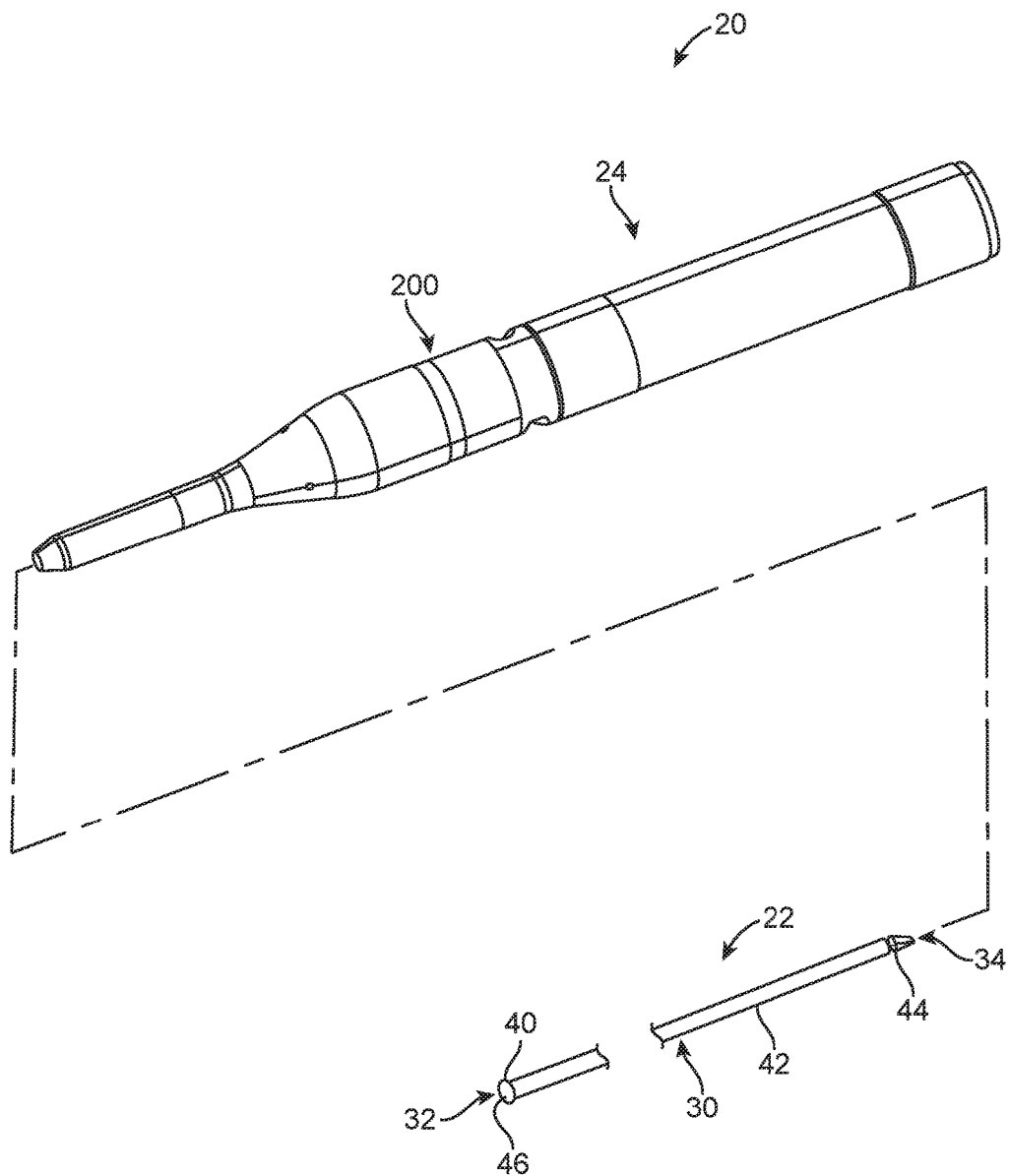
FIG. 1 is an exploded perspective view of a surgical cutting system in accordance with principles of the present disclosure.

One embodiment of a surgical cutting system 20 in accordance with principles of the present disclosure is shown in FIG. 1, and includes a rotary surgical cutting tool 22 and a powered handpiece 24. Details on the various components are described below. In general terms, the surgical cutting tool 22 is selectively coupled to the handpiece 24. Once mounted, the powered handpiece 24 is operated to rotate (e.g., rotate in a single direction or oscillate) the surgical cutting tool 22 in performing a desired surgical procedure. Aspects of the present disclosure are directed toward the coupling between the surgical cutting tool 22 and the powered handpiece 24, and in particular features provided with one or both of the surgical cutting tool 22 and the powered handpiece 24 that promote torque transmission onto the cutting tool 22 at an axis that is slanted or skewed relative to a primary central axis of the cutting tool 22. In some embodiments, aspects of the present disclosure are embodied by the surgical cutting tool 22 alone; in other embodiments, aspects of the present disclosure are embodied by the powered handpiece 24 alone; and in yet other embodiments, aspects of the present disclosure are embodied by complimentary features provided with both of the surgical cutting tool 22 and the powered handpiece 24.

In some embodiments, the surgical cutting tool 22 includes or provides an elongated shaft 30. The shaft 30 can be formed of a rigid, surgically safe material (e.g., stainless steel), and defines opposing, first and second (or distal and proximal) ends 32, 34. The shaft 30 further defines a dissection portion 40, an intermediate portion 42, and a coupling portion 44. The dissection portion 40 is provided adjacent the distal end 32, and forms or carries (e.g., has assembled thereto) a cutting head 46. The cutting head 46 can assume a wide variety of forms appropriate for performing a desired rotary surgical cutting procedure (e.g., cutting, debulking, resecting, or removing anatomical tissue including bone). By way of one non-limiting embodiment, the cutting head 46 can be a bur having any shape, size, flute pattern, etc., as desired. While the elongated shaft 30 is illustrated as being linear or straight, in other embodiments the shaft 30 can define one or more longitudinal bends or curves; in related embodiments, surgical cutting tools of the present disclosure can further include an outer sleeve (not shown) that supports a curved version of the shaft 30 as the shaft 30 is rotated.

Figure 2:
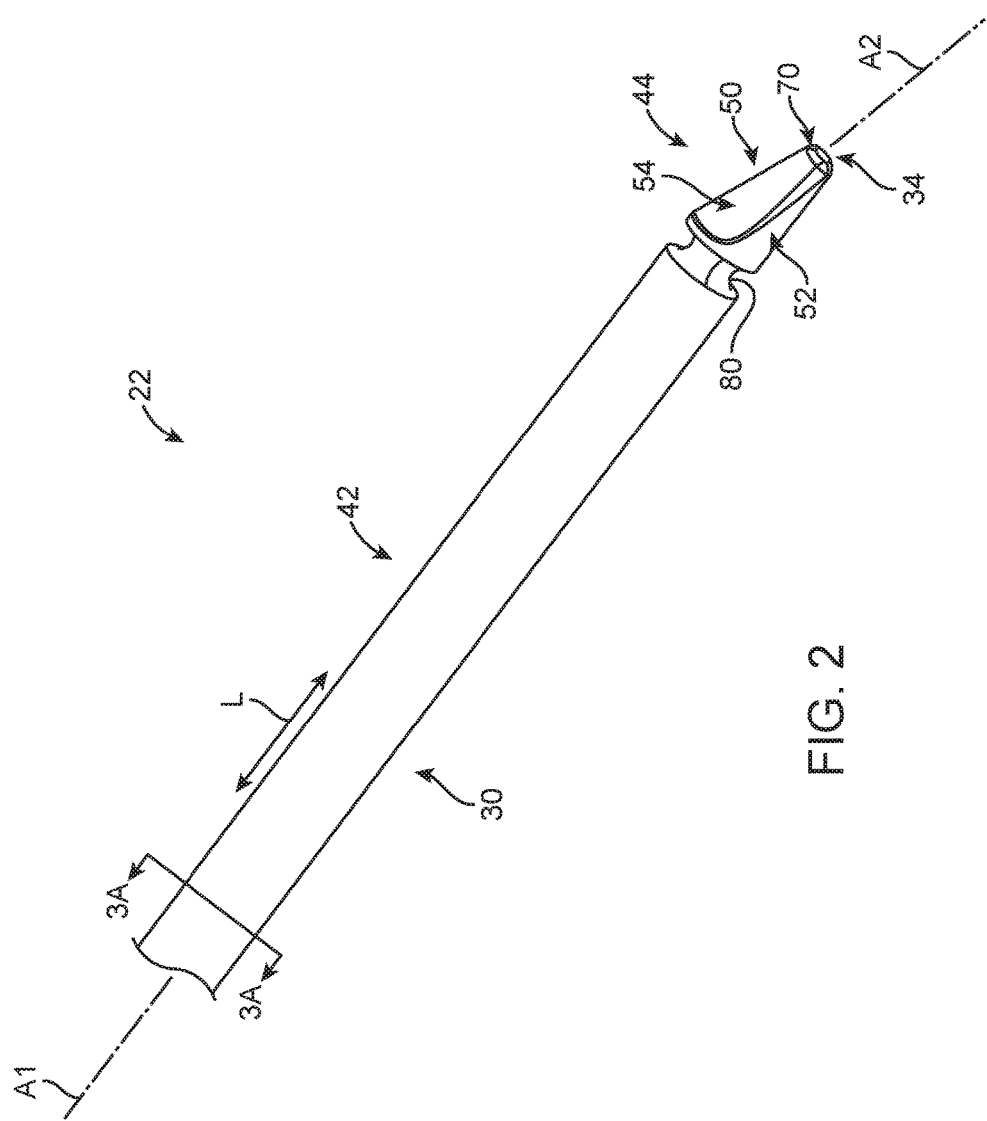
FIG. 2 is an enlarged perspective view of a portion of a surgical cutting tool in accordance with principles of the present disclosure and useful with the system of FIG. 1.
Figure 3A:
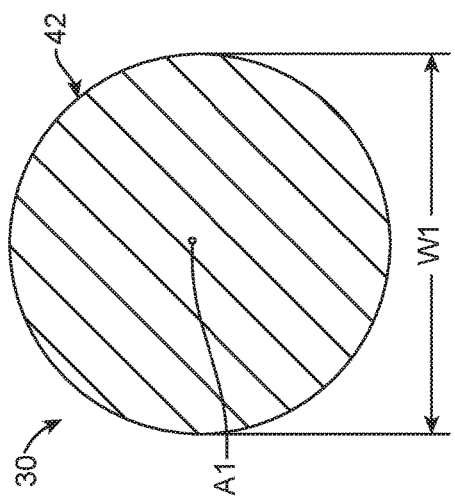
FIG. 3A is an enlarged cross-sectional view of the surgical cutting tool of FIG. 2, taken along the line 3A-3A.

One embodiment of the coupling portion 44 is shown in greater detail in FIG. 2, along with a section of the intermediate portion 42. As a point of reference, the elongated shape of the shaft 30 serves to generate a longitudinal or length direction "L", and based upon which other geometry features can be identified. The coupling portion 44 extends from the intermediate portion 42 generally in the length direction L, and terminates at the proximal end 34 of the shaft 30. At least a majority of an overall length of the shaft 30 is defined along the intermediate portion 42 (e.g., the length of the intermediate portion 42 is at least five times the length of the coupling portion 44), with a shape of the intermediate portion 42 defining a primary central axis A1 of the shaft 30. For example, the intermediate portion 42 can be cylindrical (e.g., an elongated cylinder), cylindrical-like, or have any other constant shape along at least a majority of a length of the intermediate portion 42 in a form that otherwise generates the primary central axis A1. Alternatively, and with additional reference to FIG. 3A, a shape of the intermediate portion 42 can be viewed as defining a maximum outer dimension W1 in a plane perpendicular to the length direction L (i.e., the plane of the view of FIG. 3A); because the shape reflected by FIG. 3A is a true circle, the maximum outer dimension W1 is the diameter of the circle. The primary central axis A1 intersects a center point of the maximum outer dimension W1. While the shape of the intermediate portion 42 is reflected in FIGS. 2 and 3A as being a circle (e.g., the intermediate portion 42 is an elongated right cylinder), the intermediate portion 42 can have other cross-sectional shapes that establish the maximum outer dimension W1 and that may not be truly circular in nature. In some embodiments as described in greater detail below, surface features can optionally be incorporated into the intermediate portion 42 such that an entirety of the intermediate portion 42 need not necessarily have a constant or uniform shape; however, a cross-sectional shape of the intermediate portion 42 along at least a majority of the longitudinal length L generates the primary central axis A1. The surgical cutting tool 22 is intended to rotate about the primary central axis A1 during use, with the cutting head 46 (FIG. 1) being configured to effectuate desired tissue removal when revolved about the primary central axis A1. For example, a shape or other features of the cutting head 46 can be concentric or centered about the primary central axis A1.

Figure 3B:
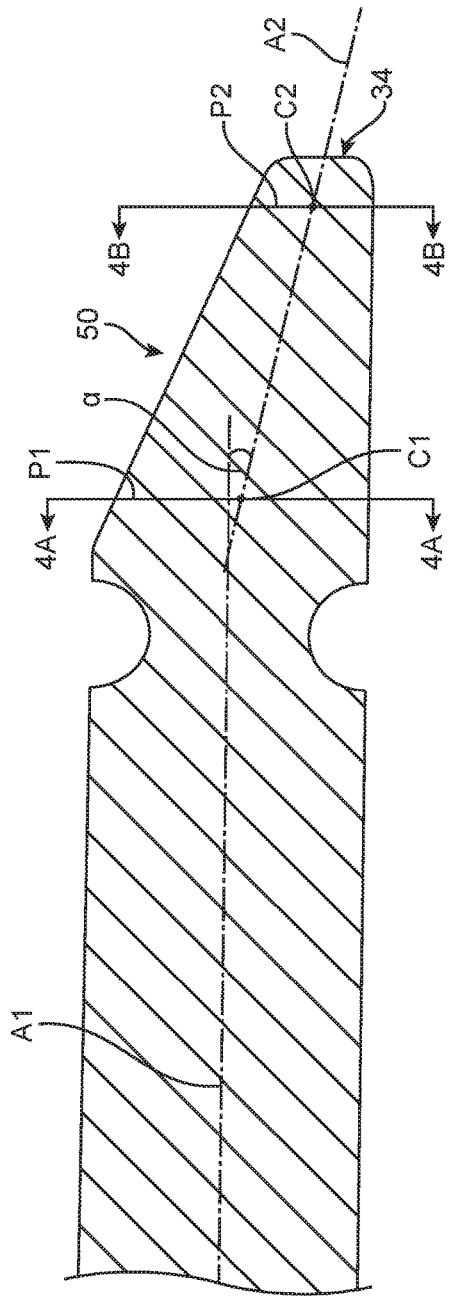
FIG. 3B is a cross-sectional view of a portion of the surgical cutting tool of FIG. 2 in a plane orthogonal to the plane of FIG. 3A.

With the above definitions in mind, and with reference to FIGS. 2 and 3B, extension of the coupling portion 44 from the intermediate portion 42 to the proximal end 34 is generally in the length direction L and includes a tang 50 configured for establishing a driven interface with the handpiece 24 (FIG. 1). A shape of the tang 50 defines a drive (or secondary) axis A2. The drive axis A2 is slanted relative to the primary central axis A1, thereby establishing the tang 50 as an off-axis drive component. The tang 50 can be sized and shaped to create the drive axis A2 in a various manners as described below. In general terms, however, the tang 50 serves to transfer torque from the handpiece 24 to the cutting tool 22, with the slanted arrangement of the drive axis A2 relative to the primary central axis A1 creating a crank shaft-like drive relationship in which a drive or input torque received at the tang 50 is effectively off-set from the primary central axis A1 and is transmitted or transferred to the intermediate portion 42, and thus a remainder of the cutting tool 22, as a torque about the primary central axis A1. With this configuration, the cutting tool 22 exhibits elevated strength (as compared to conventional rotary-type cutting tools in which the input force is applied purely about the corresponding primary central axis) as the tang 50 is driven by a shear force (as compared to a conventional line contact force interface), and point load stresses are reduced.

The drive axis A2 is generated by a perimeter shape of the tang 50. In particular, the tang 50 has a tapered cylindrical shape, tapering in outer dimension in a direction of the proximal end 34. As used throughout the present disclosure, the term "tapered cylindrical shape" is specifically inclusive of a non-symmetrically tapered cylindrical shape and a symmetrically tapered cylindrical shape. The drive axis A2 passes through a centroid of at least two, spaced apart cross-sectional planes of the tang 50 taken along the tapering shape and perpendicular to the primary central axis A1. Two such spaced apart planes are identified in FIG. 3B as "P1" and "P2"; a spatial relationship of the first and second planes P1, P2 relative to one another and relative to an end-use orientation of the cutting tool 22 is such that the first plane P1 can be referenced as a "distal" plane, and second plane P2 as a "proximal" plane. A centroid C1 of the tang 50 in the distal plane P1 is identified, as is a centroid C2 in the proximal plane P2. By way of further clarification, a perimeter shape of the tang 50 at the distal plane P1 and from which the centroid C1 is derived is further illustrated in FIG. 4A, whereas FIG. 4B reflects the perimeter shape at the proximal plane P2 and the corresponding centroid C2. With specific reference to FIG. 3B, the drive axis A2 passes through the centroids C1, C2 and is slanted with respect to the primary central axis A1. In other words, the drive axis A2 is oblique with respect to the primary central axis A1. As further identified in FIG. 3B, a slant angle α is formed at an intersection of the primary and drive axes A1, A2, and in some embodiments is in the range of 1-89 degrees, optionally in the range of 2-30 degrees, and in other embodiments is in the range of 3-20 degrees.

Figure 5:
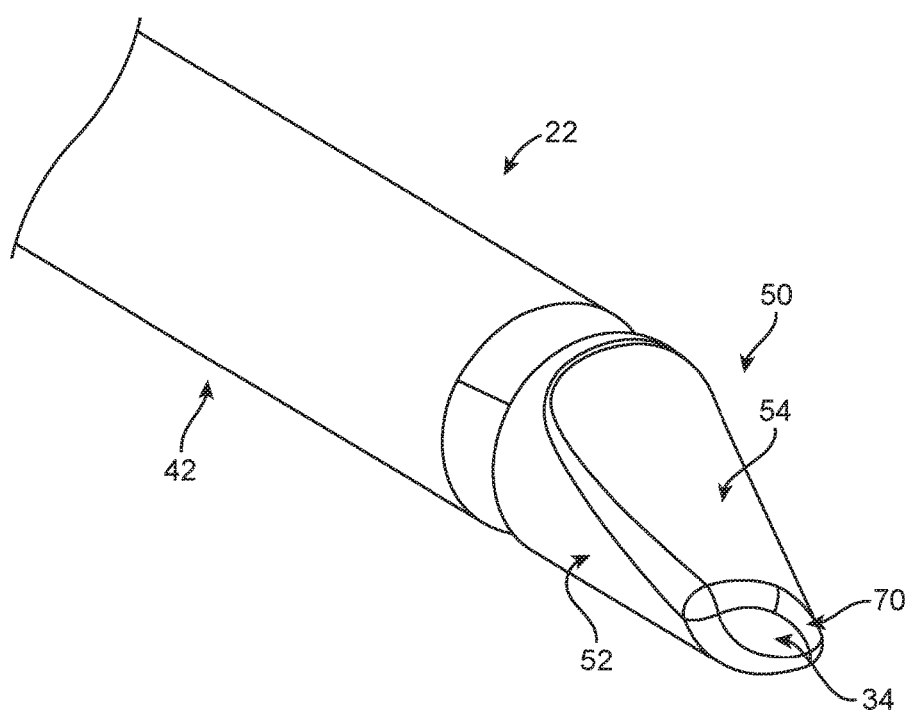
FIG. 5 is an enlarged perspective end view of a portion of the surgical cutting tool of FIG. 2.

In some embodiments, the tapered cylindrical shape is continuous along at least a majority of the tang 50 (relative to the length direction L), and can be characterized by the tang 50 having continuously curved surfaces in a transverse cross-sectional plane (perpendicular to the primary central axis A1). For example, a shape of the tang 50 can be generated by machining or grinding a curved surface into a right cylinder. The enlarged view of FIG. 5 reflects this approach, whereby surfaces of the tang 50 effectively include or define a first partial cylinder region 52 and a second partial cylinder region 54 that combine to form the tang 50 has optionally having a non-symmetrical tapered cylindrical shape. In other embodiments, the tangs of the present disclosure can have a symmetrical tapered cylindrical shape. The first partial cylinder region 52 is akin to a right cylinder (i.e., a portion of a night cylinder) and is a continuation of the right cylinder shape of the intermediate portion 42. The second partial cylinder region 54 is machined or cut into the right cylinder shape associated with the first region 52, and is akin to a tapered cylinder. An axial centerline of the shape of the second partial cylinder region 54 is slanted relative to the axial centerline of the shape of the first partial cylinder region 52.

Figure 4A:
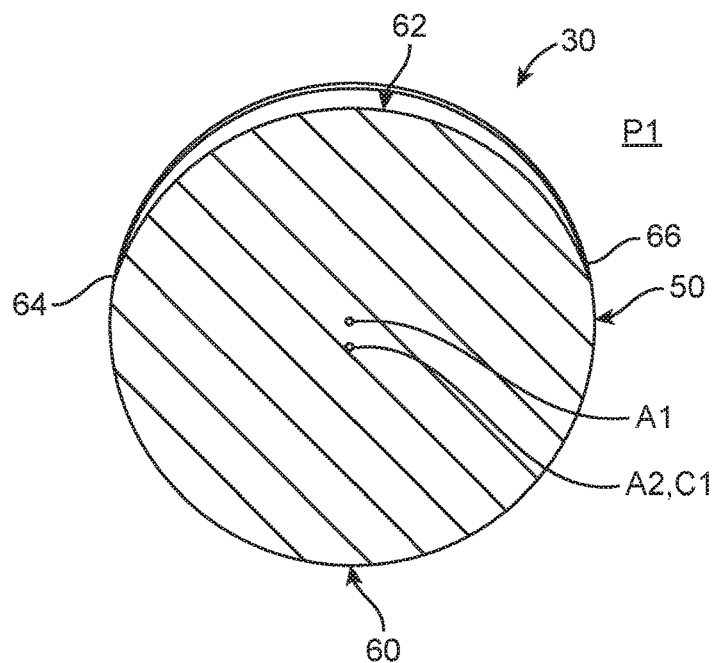
FIG. 4A is an enlarged cross-sectional view of the surgical cutting tool of FIG. 3B, taken along the line 4A-4A.
Figure 4B:
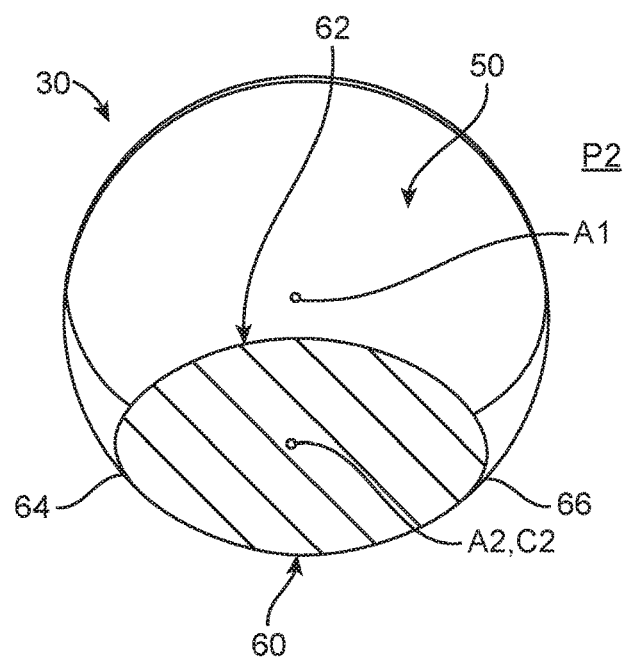
FIG. 4B is an enlarged cross-sectional view of the surgical cutting tool of FIG. 3B, taken along the line 4B-4B.
Figure 6:
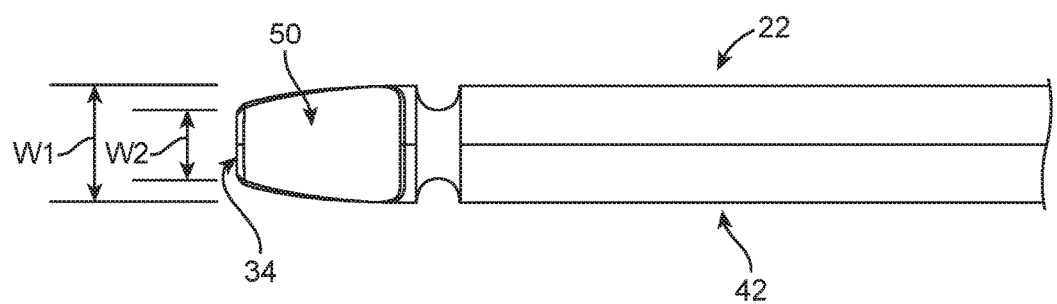
FIG. 6 is a top plan view of a portion of the surgical cutting tool of FIG. 2.

The tapered cylindrical shape, optionally non-symmetrical tapered cylindrical shape, of the tang 50 can also be described with reference to a perimeter shape in transverse cross-section. With reference to FIG. 4A, a transverse cross-sectional perimeter shape (i.e., in the distal plane P1 that is otherwise perpendicular to the primary central axis A1) along at least a portion of the tang 50 can be characterized as including a first segment 60 opposite a second segment 62. The first segment 60 is generated by the first partial cylinder region 52 (best seen in FIG. 5), and the second segment 62 is generated by the second partial cylinder region 54. The first and second segments 60, 62 are each continuously curved (e.g., arcs or convex curves), and intersect at opposing lines of intersection 64, 66. A radius of curvature of the first segment 60 can be substantially identical to a radius of curvature of the intermediate portion 42 (as represented by the transverse cross-section of FIG. 3A), and reflects that the first segment 60 of the shape of the tang 50 is a continuation of the shape of the intermediate portion 42 (i.e., the tang 50 does change in shape relative to a shape of the intermediate portion 42 along the first partial cylinder region 64). A radius of curvature of the second segment 62 can be the same as or greater than that of the first segment 60. An arc length of the second segment 62 (i.e., distance along the second segment 62 from the first line of intersection 64 to the second line of intersection 66) is less than an arc length of the first segment 60 and reflects the tapering nature of the tang 50. FIG. 4B is another transverse cross-section of the tang 50 (in the proximal plane P2 that again is perpendicular to the primary central axis A1) at a location closer to the proximal end 34 (FIG. 2) as compared to a location of the cross-section of FIG. 4A. The continuously curved, first and second segments or arcs 60, 62 are again evident in the view of FIG. 4B, as are the opposing lines of intersection 64, 66. A comparison of FIGS. 4A and 4B reveals that the radius of curvature of the first segment 60 is substantially identical (i.e., within 5% of a truly identical relationship); however, the tapered shape of the tang 50 is such that the arc length of the first segment 60 has decreased in a direction of the proximal end 34 (FIG. 2) (i.e., the arc length of the first segment 60 at the location of the cross-sectional view of the distal plane P1 of FIG. 4A is greater than the arc length of the first segment 60 in FIG. 4B). A radius of curvature of the second segment 62 (again, in a plane perpendicular to the primary central axis A1) can be identical or can increase in a direction of the proximal end 34 (i.e., the radius of curvature of the second segment 62 at the location of the distal plane P1 cross-section of FIG. 4A can be less than the radius of curvature of the second segment 62 at the proximal plane P2 of FIG. 4B). An arc length of the second segment 62 also decreases in a direction of the second end 34; the arc length of the second segment 62 at the location of the proximal plane P2 cross-section of FIG. 4B is less than the arc length of the second segment 62 at the location of the distal plane P1 cross-section of FIG. 4A. Because the arc lengths of the first and second segments 60, 62 decrease in a direction of the proximal end 34, a maximum outer dimension of the tang 50 tapers in a direction of the proximal end 34. This relationship is highlighted by the view of FIG. 6 whereby the maximum outer dimension W1 of the tang 50 proximate the intermediate portion 42 is greater than the maximum outer dimension proximate the proximal end 34 (identified as W2).

The geometry characterizations of the tapered cylindrical shape of the tang 50 described above may or may not be continuous. For example, with the embodiment of FIGS. 2 and 5, the various surfaces of the tang 50 (e.g., surfaces of the first and second partial cylinder regions 52, 54) are substantially smooth and contiguous from a location proximate the intermediate portion 42 to a location proximate the proximal end 34. In other embodiments, minor interruptions can be incorporated into one or more of the surfaces as described below. In more general terms, the tapered cylindrical shape of the tangs of the present disclosure (such as the non-symmetrically tapered cylindrical shaped tang 50) is characterized by a perimeter shape in a transverse cross-sectional plane (perpendicular to the primary central axis A1) having two continuously curved segments (or arcs) combining to define a substantial majority (e.g., at least 80%) of the shape's perimeter length; further, this geometry is found at least at two spaced apart locations (i.e., distal and proximal locations or planes, such as the distal and proximal planes P1, P2 mentioned above) along a length of the tang, with an arc length of each of the two segments at the distal plane or location being greater than that at the proximal plane or location.

In some embodiments, the above-described geometry of the tang 50 can continue to the proximal end 34. In other embodiments, the coupling portion 44 can include a trailing section 70 extending between the tang 50 and the proximal end 34. Geometry of the trailing section 70 can be akin to the tang 50, but generally tapers (in the length direction L) in all directions to the proximal end 34 as shown. Thus, the trailing section 70 can be concentric about the drive axis A2, and can have a conical shape that promotes self-alignment with corresponding components of the powered handpiece 24 (FIG. 1). Other shapes conducive to self-alignment are also acceptable.

As alluded to above, the surgical cutting tools 22 of the present disclosure optionally include or define one or more axial retention features that serve to effectuate an axial "lock" of the tool 22 when fully inserted into the powered handpiece 24 (FIG. 1). The axial retention feature, where provided, can assume various forms and is typically designed in tandem with corresponding components provided with the powered handpiece 24. For example, in the exemplary embodiment of FIG. 2, an axial retention feature is provided as a circumferential groove 80 in the coupling portion 44 immediately adjacent the intermediate portion 42 (i.e., the axial retention feature 80 is distal the tang 50). The axial retention feature can alternatively be one or more notches, flats, holes, troughs, a biased mechanism, etc., and can be located elsewhere along the coupling portion 44 and/or along the intermediate portion 42. In yet other embodiments, the axial retention feature can be omitted.

Figure 7:
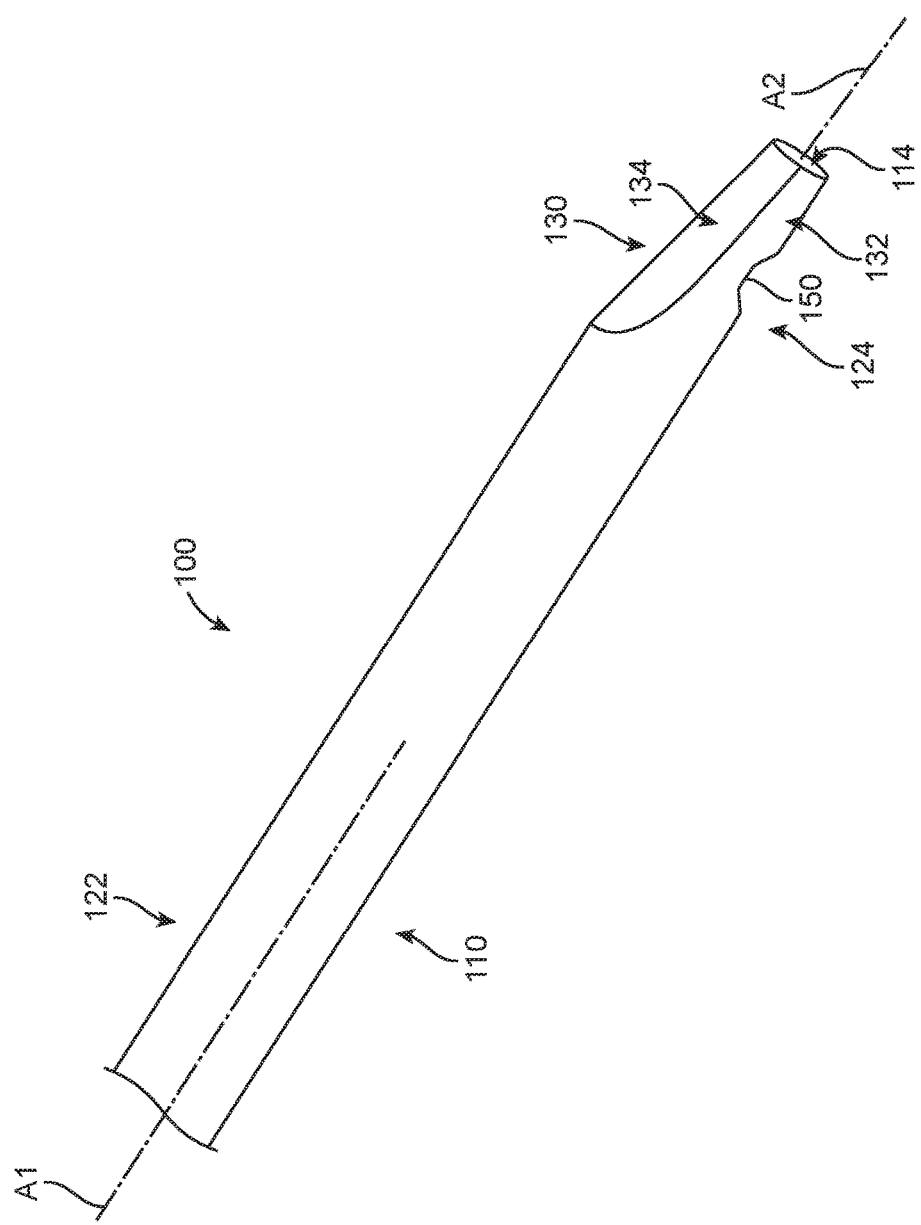
FIG. 7 is a simplified perspective view of a portion of another surgical cutting tool in accordance with principles of the present disclosure.

The surgical cutting tools of the present disclosure can incorporate other geometries establishing the slanted drive axis A2. For example, FIG. 7 illustrates portions of another embodiment surgical cutting tool 100 in accordance with principles of the present disclosure. The cutting tool 100 includes an elongated shaft 110 that defines a first (or distal) end (not shown) opposite a second (or proximal) end 114. The shaft 110 further defines a dissection portion (not shown), an intermediate portion 122, and a coupling portion 124. The dissection portion and the intermediate portion 122 can assume any of the forms described above. In this regard, the intermediate portion 122 is generally sized and shaped to define a primary central axis A1 as further identified in the cross-sectional view of FIG. 8A. The coupling portion 124 extends from the intermediate portion 122 and includes a tang 130. The tang 130 is sized and shaped to define a drive axis A2, with the drive axis A2 being slanted with respect to the primary central axis A1 commensurate with the descriptions above.

In particular, an outer shape of the tang 130 is, or is akin to, a tapered cylinder, tapering in outer dimension in a direction of the proximal end 114. The drive axis A2 passes through a centroid of at least two, spaced apart cross-sectional planes of the tang 130 taken along the tapering shape and perpendicular to the primary central axis A1. Two such spaced apart planes are identified in FIG. 8A as "P1" (distal plane) and "P2" (proximal plane). A centroid C1 of the tang 130 in the distal plane P1 is identified, as is a centroid C2 in the proximal plane P2. By way of further clarification, a perimeter shape of the tang 130 at the distal plane P1 and from which the centroid C1 is derived is further illustrated in FIG. 8B, whereas FIG. 8C reflects the perimeter shape at the proximal plane P2 and the corresponding centroid C2. The drive axis A2 passes through the centroids C1, C2 and is slanted with respect to the primary central axis A1, with a slant angle α formed at an intersection of the primary and drive axes A1, A2 as described above.

In some embodiments, the tapered cylindrical shape of the tang 130 can be generated by machining or grinding a curved surface into a right cylinder. For example, FIG. 7 identifies a shape of the tang 130 as defining or including a first partial cylinder region 132 and a second partial cylinder region 134. The first partial cylinder region 132 is akin to a right cylinder (i.e., a portion of a right cylinder) and is a continuation of the right cylinder shape of the intermediate portion 122. The second partial cylinder region 134 is machined or cut into the right cylinder shape associated with the first partial cylinder region 132, and can be akin to a right cylinder or a tapered cylinder. An axial centerline of the second partial cylinder region 134 is slanted relative to the axial centerline of the shape of the first partial cylinder region 132. The first and second partial cylinder regions 132, 134 combine to generate the tapered cylindrical shape of the tang 130 as a non-symmetrical tapered cylindrical shape; in other embodiments, the tapered cylindrical shape can be a symmetrical tapered cylindrical shape.

Figure 8B:
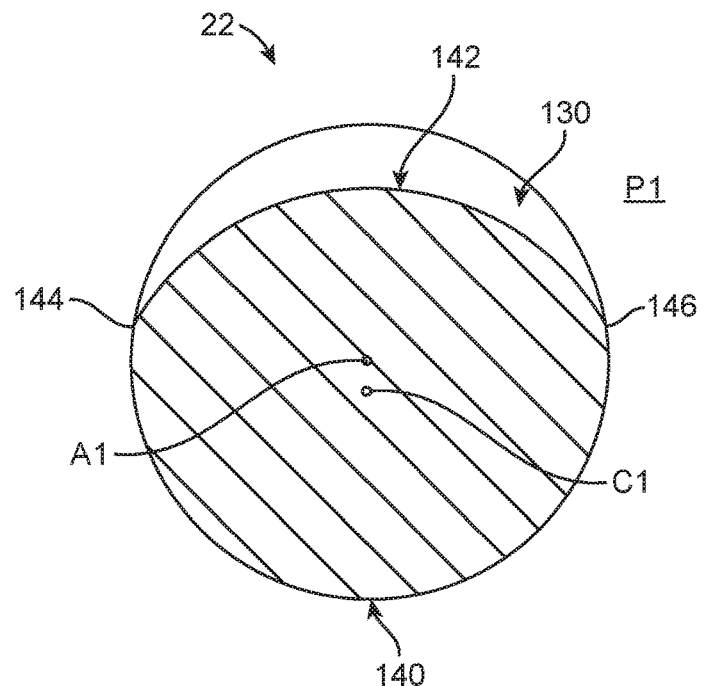
FIG. 8B is an enlarged cross-sectional view of the surgical cutting tool of FIG. 8A, taken along the line 8B-8B.
Figure 8C:
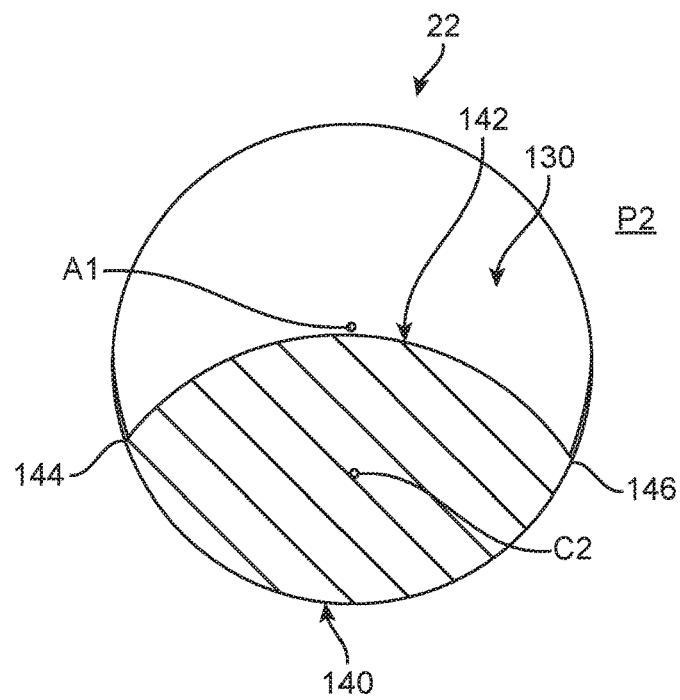
FIG. 8C is an enlarged cross-sectional view of the surgical cutting tool of FIG. 8A, taken along the line 8C-8C.

The tapered cylindrical shape of the tang 130 can also be described with reference to a perimeter shape in transverse cross-section. With reference to FIG. 8B, a transverse cross-sectional perimeter shape (i.e., in the distal plane P1 that is otherwise perpendicular to the primary central axis A1) along at least a portion of the tang 130 can be characterized as including a first segment 140 opposite a second segment 142. The first segment 140 is generated by the first partial cylinder region 132 (best seen in FIG. 7), and the second segment is generated by the second partial cylinder segment 134. The first and second segments 140, 142 are continuously curved (e.g., arcs or convex curves), and intersect at opposing lines of intersection 144, 146. A radius of curvature of the first segment 140 can be substantially identical to a radius of curvature of the intermediate portion 122 (FIG. 7), and reflects that the first segment 140 of the shape of the tang 130 is a continuation of the shape of the intermediate portion 122. The radius of curvature of the second segment 142 can be the same as or greater than that of the first segment 140. An arc length of the second segment (i.e., distance along the second segment 142 from the first line of intersection 144 to the second line of intersection 146) is less than an arc length of the first segment 140, and reflects the tapering nature of the tang 130 in a direction of the proximal end 114 (FIG. 7). FIG. 8C is another transverse cross-section of the tang 130 (in the proximal plane P2 that again is perpendicular to the primary central axis A1) at a location closer to the proximal end 114 as compared to a location of the cross-section of FIG. 8B. The continuously curved, first and second segments 140, 142 and lines of intersection 144, 146 are again evident in the view of FIG. 8C. A comparison of FIGS. 8B and 8C reveals that the radius of curvature of the first segment 140 is substantially identical (i.e., within 5% of a truly identical relationship); however, the tapered shape of the tang 130 is such that an arc length of the first segment 140 has decreased in a direction of the proximal end 114 (i.e., the arc length of the first segment 140 at the location of the cross-sectional view of FIG. 8B is greater than the arc length of the first segment 140 in FIG. 8C). A radius of curvature of the second segment 142 (again, in a plane perpendicular to the primary central axis A1) can be identical or can increase in a direction of the second end 114 (i.e., the radius of curvature of the second segment 142 at the location of the distal plane P1 cross-sectional of FIG. 8B can be less than the radius of curvature of the second segment 142 at the proximal plane P2 of FIG. 8C). An arc length of the second segment 142 has decreased in a direction of the proximal end 114; the arc length of the second segment 142 at the location of the proximal plane P2 cross-section of FIG. 8C is less than the arc length of the second segment 142 at the location of the distal plane P1 cross-section of FIG. 8B. Because the arc lengths of the segments 140, 142 decrease in a direction of the proximal end 114, a maximum outer dimension of the tang 130 tapers in a direction of the proximal end 114 as described above.

Figure 8D:
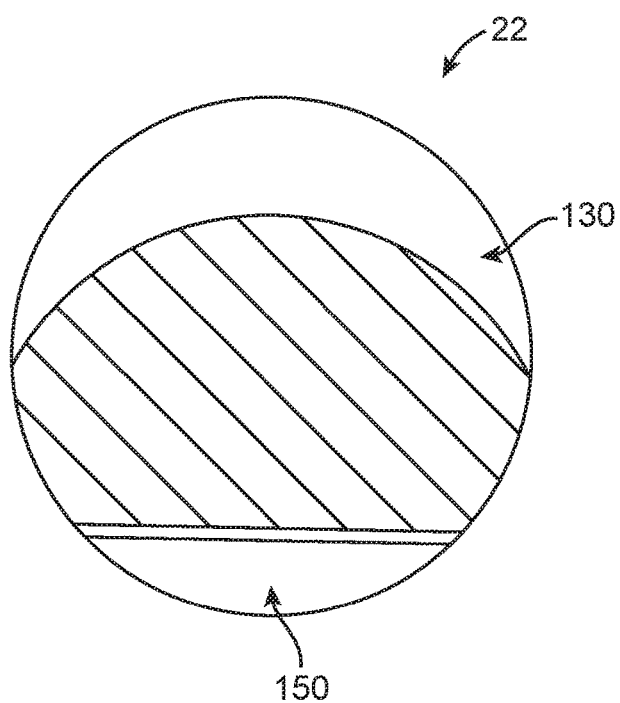
FIG. 8D is an enlarged cross-sectional view of the surgical cutting tool of FIG. 8A, taken along the line 8D-8D.

Returning to FIGS. 7 and 8A, the coupling portion 124 optionally includes or provides an axial retention feature in the form of a slot 150 defined along a portion of the tang 130. For example, the slot 150 can be cut (e.g., tangent to the primary central axis A1) into a surface of the first partial cylinder region 132. In some embodiments, the tapering shape of the tang 130 along the second partial cylinder region 134 is free of any surface alterations. A cross-sectional perimeter shape of the tang 130 in a plane perpendicular to the primary central axis A1 at a location of the slot 150 is reflected by FIG. 8D. While geometries of the perimeter transverse cross-sectional shape of the tang 130 at the slot 150 may deviate from other sections of the tang 130 (e.g., a region of the perimeter shape in the cross-section of FIG. 8D is linear), the tang 130 overall has the tapered cylindrical shape in accordance with principles of the present disclosure; namely, in the spaced apart, transverse cross-section (perpendicular to the primary central axis A1) locations of FIGS. 8B and 8C, the perimeter shape includes two continuously curved segments (or arcs) 140, 142 combining to define a substantial majority (e.g., at least 80%) of the shape's perimeter length, and an arc length of each of the two segments 140, 142 at the distal plane or location P1 is greater than that at the proximal plane or location P2.

Returning to FIG. 1, the powered handpiece 24 includes one or more features configured to interface with the surgical cutting tools of the present disclosure, including the slanted axis tang, in selectively receiving/loading the surgical cutting tool and for rotatably driving a loaded surgical cutting tool. In this regard, the powered handpieces of the present disclosure can employ various drive assemblies or motors (e.g., pneumatically powered or driven, electrically powered or driven, etc.) as known in the art for effectuating driven rotation at desired speeds, and generally include a housing assembly 200 maintaining a drive shaft (not shown) that mechanically couples or links a motor (not shown) to a drive chuck or collet via a coupling assembly. The drive chuck, in turn, is configured to receive the proximal pin region of the corresponding surgical cutting tool.

Figure 9A:
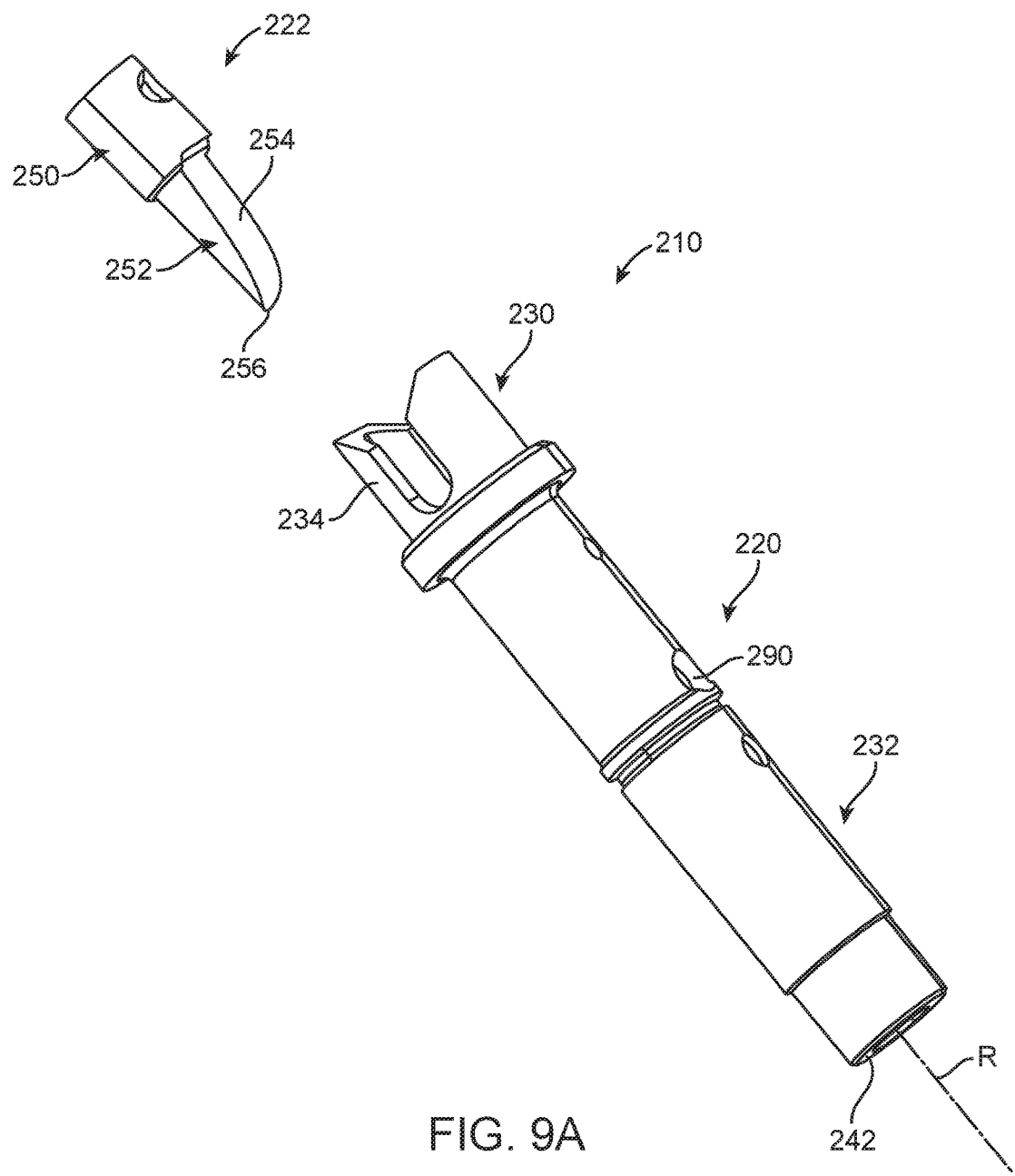
FIG. 9A is an exploded perspective view of a drive chuck useful with a powered handpiece of the system of FIG. 1.
Figure 9B:
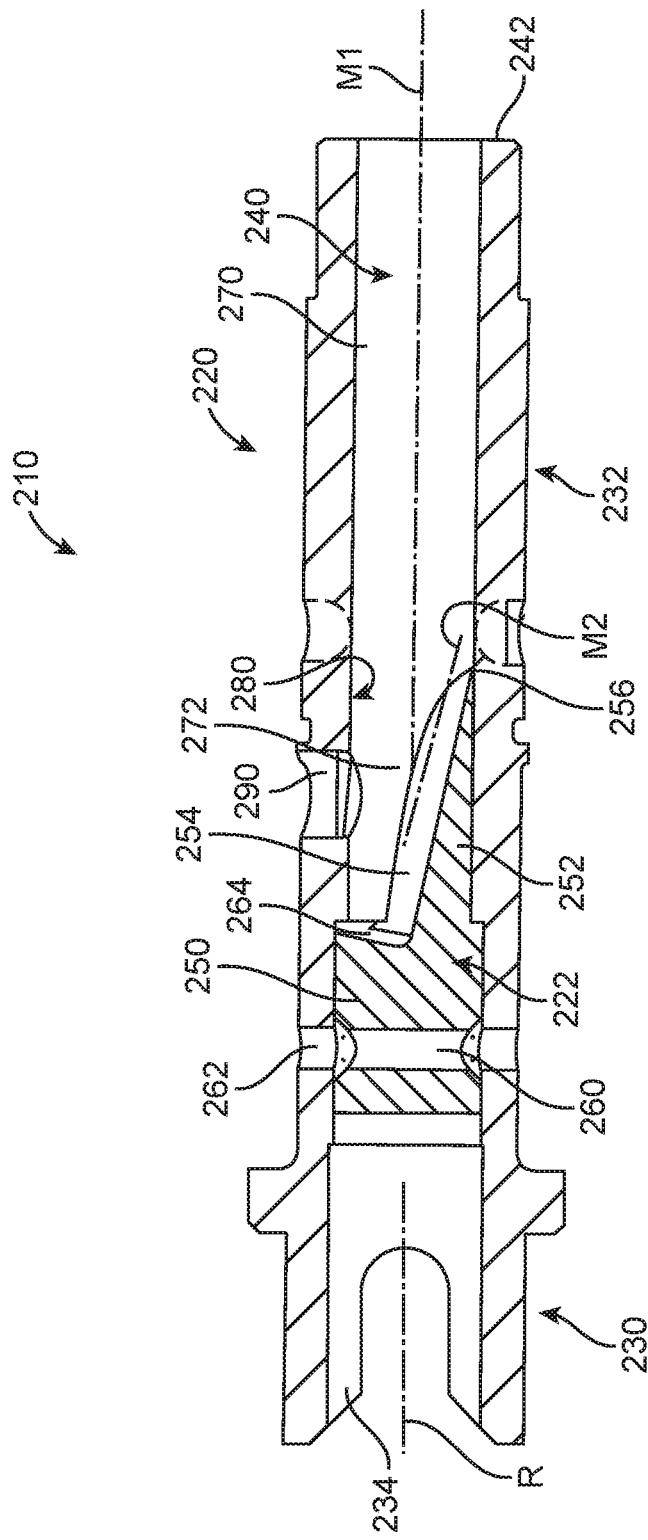
FIG. 9B is a longitudinal cross-sectional view of the drive chuck of FIG. 9A upon final assembly.

For example, one embodiment of a drive chuck 210 in accordance with principles of the present disclosure and useful with the surgical cutting tool 100 (FIG. 7) is shown in FIGS. 9A and 9B. In some constructions, the drive chuck 210 can be constructed from two (or more) primary components, including a drive chuck body 220 and an interface member 222. The drive chuck body 220 has an elongated shape, and generally forms or defines a drive shaft region 230 and a tool region 232. The drive shaft region 230 is generally configured for mounted assembly to a drive shaft (not shown) component of the powered handpiece 24 (FIG. 1) in a manner that creates a rigid coupling there between. For example, the drive shaft region 230 can include or form a socket 234 or similar structure adapted for coupled engagement with the drive shaft. Any other coupling assembly construction is equally acceptable. In yet other embodiments, the drive chuck 210 and the drive shaft can be integrally formed as a single, homogenous part. Regardless, an axis of rotation R is established at the drive shaft region 230 when coupled to the drive shaft, and about which the drive chuck 210 will rotate when driven by the drive shaft.

The interface member 222 is configured for assembly within the drive chuck member 220 and combines with the tool region 232 to provide various features (e.g., surfaces) configured to receive and engage the surgical cutting tool 100 (FIG. 7), and in particular the tang (e.g., the tang 130 (FIG. 7)) and at least a portion of the intermediate portion. With this in mind, the tool region 232 can be a generally tubular body defining a passage 240. The passage 240 is open at a distal end 242 of the drive chuck member 220. A major central axis M1 is established by a shape of the passage 240, and is aligned with the axis of rotation R.

The interface member 222 includes or defines a base 250 and a head 252. The base 250 is configured for assembly to the drive chuck member 220 as described below, whereas the head 252 generates an engagement surface 254 in extension from the base 250 to a leading end 256. For reasons made clear below, a diameter (or other maximum outer dimension) of the base 250 is greater than that of the head 252. The engagement surface 254 is sized and shaped in accordance with a size and shape of a portion of the cutting tool's tang 130 (FIG. 7).

More particularly, and with specific reference to FIG. 9B, upon final assembly, the head 252 projects into the passage 240 opposite the distal end 242. Assembly of the interface member 222 to the drive chuck member 220 can be accomplished in a variety of manners, for example via a pin (not shown) passing through a bore 260 in the base 250 and holes 262 in the drive check member 220. Regardless, the base 250 is aligned with the major central axis M1 and is sized to be larger than a diameter of the passage 240. Thus, the base 250 effectively establishes a proximal end 264 of the passage 240, with projection of the head 252 into the passage 240 serving to define guide zone 270 and an engagement zone 272 along the passage 240. The guide zone 270 extends from the open distal end 242 and is sized and shaped in accordance with the corresponding surgical cutting tool's intermediate portion (e.g., the intermediate portion 122 of FIG. 7). For example, with embodiments in which a shape of the intermediate portion 122 is akin to a right cylinder, the passage 240 along the guide zone 270 is cylindrical and has a diameter approximating a diameter of the intermediate portion 122 such that the intermediate portion 122 can be freely received within the guide zone 270.

The engagement zone 272 extends from the guide zone 270, and is sized and shaped in accordance with a size and shape of the cutting tool's tang (e.g., the tang 130 of FIG. 7). The engagement surface 254 and an interior surface 280 of the drive chuck member 220 not otherwise "covered" by the interface member 222 combine to define the shape of the engagement zone 272. In this regard, a shape of the interior surface 280 is akin to a right cylinder. The engagement surface 254 has an arc-like shape in transverse cross-section, and is progressively spaced away from the major central axis M1 in extension to the leading end 256. A shape of the passage 240 along the engagement zone 272 establishes a secondary central axis M2 that is slanted with respect to the major central axis M1 in an identical manner as with the primary and drive axes A1, A2 (FIG. 8A) of the surgical cutting tool 100 (FIG. 7) as described above.

In some embodiments, the surgical tools of the present disclosure include an optional axial retention feature(s). Commensurate with these non-limiting constructions, the drive chuck 210 can optionally provide one or more features that promote a desired interface with the surgical tool axial retention feature(s). For example, FIGS. 9A and 9B reflect that one or more holes 290 can be defined in the drive chuck member 220 and that are open to the passage 240. As described in greater detail below, the hole(s) 290 is sized to retain a capture body (not shown), such as a ball, and is located relative to a longitudinal length of the passage 240 such that the so-retained capture body interfaces with the axial retention feature of the surgical cutting tool upon complete insertion into the drive chuck 210. A wide variety of other axial retention configurations are equally acceptable, and the drive chuck 210 can be configured accordingly (e.g., may or may not include the hole(s) 290).

While the interface member 222 has been illustrated and described as being a component formed apart from, and assembled to, the drive check member 220, in other embodiments, the drive chuck 210 can be an integrally formed body (e.g., the surface features presented by the engagement surface 254 along the engagement zone 272 can be machined into a singular, homogenous material block).

Figure 10A:
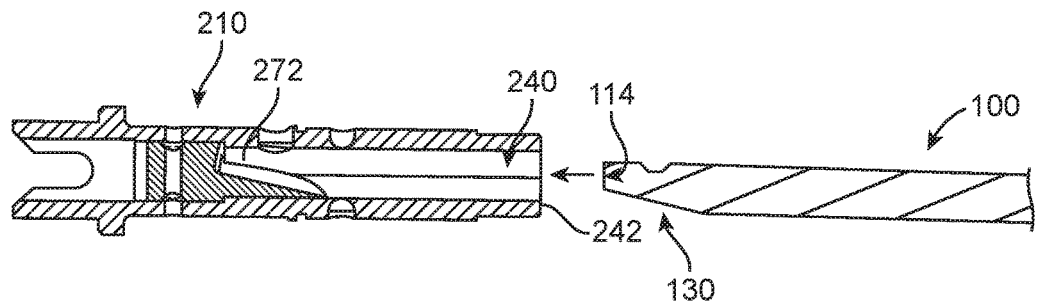
FIGS. 10A-10C illustrate insertion of the surgical cutting tool of FIG. 7 into the drive chuck of FIG. 9A.
Figure 10B:
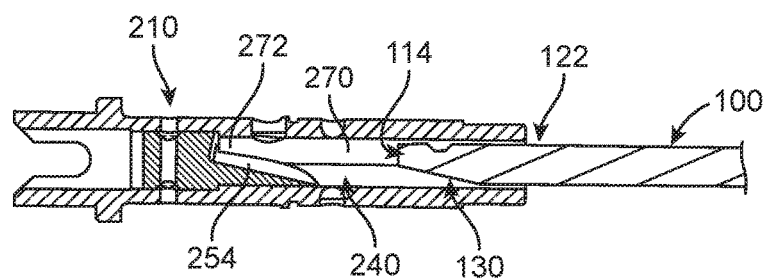
Figure 10C:
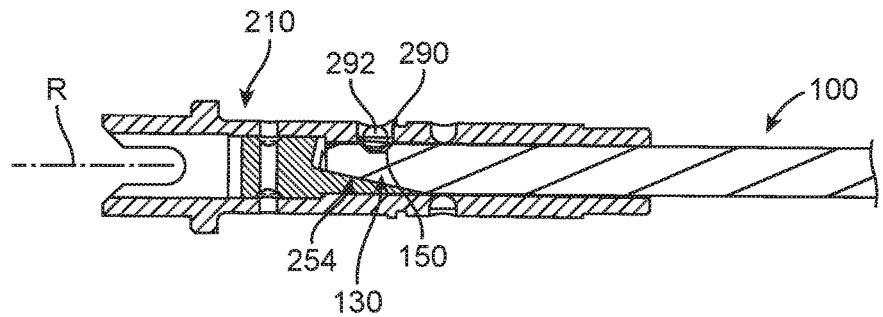

Insertion of the surgical cutting tool 100 into the drive chuck 210 is shown in FIGS. 10A-10C. It will be understood that the powered handpiece 24 (FIG. 1) can include multiple other components that interface with the surgical cutting tool 22 and/or support the drive chuck 210 (and other components mounted to the drive chuck 210, such as a drive shaft); for ease of understanding, the views of FIGS. 10A-10C illustrate the drive chuck 210 and the surgical cutting tool 100 in isolation.

In the arrangement of FIG. 10A, the surgical cutting tool 100 is poised for insertion into the drive chuck 210 (it being understood that at the stage of insertion reflected by FIG. 10A, the surgical cutting tool 100 may previously have been inserted into other components of the powered handpiece 24 (FIG. 1) that serve to guide the surgical cutting tool 100 toward the drive chuck 210). More particularly, the proximal or second end 114 is longitudinally or axially aligned with the passage 240 at the open distal end 242. The tang 130 may or may not be rotationally aligned with the engagement zone 272.

As the surgical cutting tool 100 is moved toward the drive chuck 210 (and/or vice-versa) in the direction of the arrow of FIG. 10A, the proximal end 114 enters the passage 240 and traverses along the guide zone 270 to the arrangement of FIG. 10B. The intermediate portion 122 contacts surfaces of the drive chuck 210 along the guide zone 270, ensuring that the surgical cutting tool 100 is generally aligned relative to the passage 240. With continued insertion of the surgical cutting tool 100, the tang 130 approaches and then enters the engagement zone 272. At this stage of the insertion process (i.e., immediately prior to the proximal end 114 entering the engagement zone 272), the tang 130 may or may not be rotationally aligned with the engagement zone 272. That is to say, while FIG. 10B reflects that the user happened to spatially arrange the surgical cutting tool 100 relative to the drive chuck 210 such that the tang 130 was aligned with the engagement zone 272, in most scenarios, the tang 130 will not be precisely aligned with the engagement zone 272 upon initial insertion. However, the tapered conical shape of the tang 130 promotes self-alignment into the engagement zone 272 as the surgical cutting tool 100 is inserted into the drive chuck 210. Even if misaligned, the smaller diameter (or other maximum outer dimension) proximal end 114 will readily come into sliding contact with the engagement surface 254; this sliding interface has a cam-like effect, causing the surgical cutting tool 100 to rotate with further insertion and bringing the tang 130 into alignment with the engagement zone 272. Complete insertion of the surgical cutting tool 100 into the drive chuck 210 is shown in FIG. 10C. The tang 130 is in flush engagement or contact with the engagement surface 254.

As mentioned above, the systems of the present disclosure can optionally be configured to provide for an axial lock between the surgical cutting tool 100 and the drive chuck 210 upon final insertion. FIG. 10C reflects one optional embodiment in which the surgical cutting tool 100 provides an axial retention feature in the form of the slot 150. With this non-limiting design, the drive chuck 210 can optionally include the hole(s) 290 that is otherwise aligned with the slot 150 in the inserted state. A capture body 292, such as a ball, is maintained with the corresponding hole 290 and is lodged within the slot 150 to axially "lock" the surgical cutting tool 100 relative to the drive chuck 210. It will be understood that the powered handpiece 24 (FIG. 1) can include additional components that bias the capture body 292 to the engaged state of FIG. 10C. A wide variety of other axial retention constructions or mechanisms can alternatively be employed.

Figure 11A:
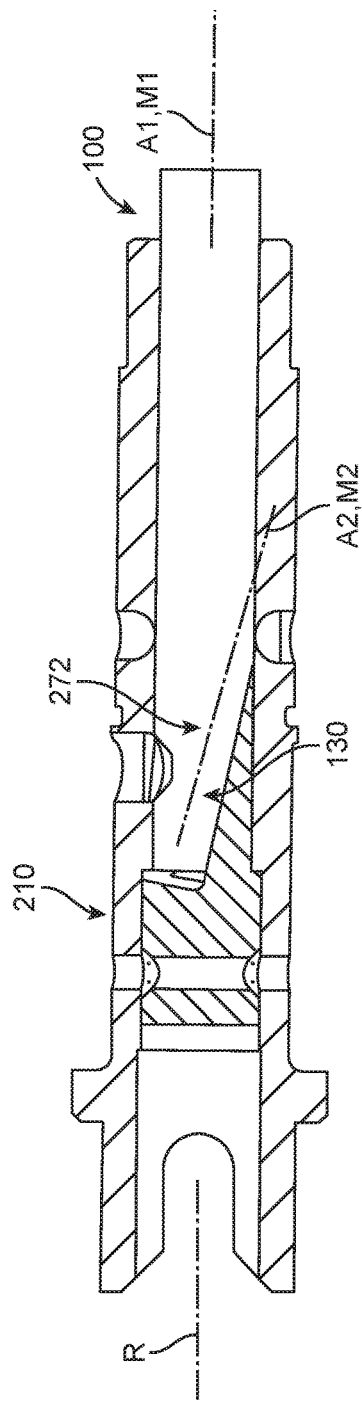
FIGS. 11A and 11B are simplified functional diagrams illustrating force transmission from a drive chuck to a surgical cutting tool in accordance with principles of the present disclosure.
Figure 11B:
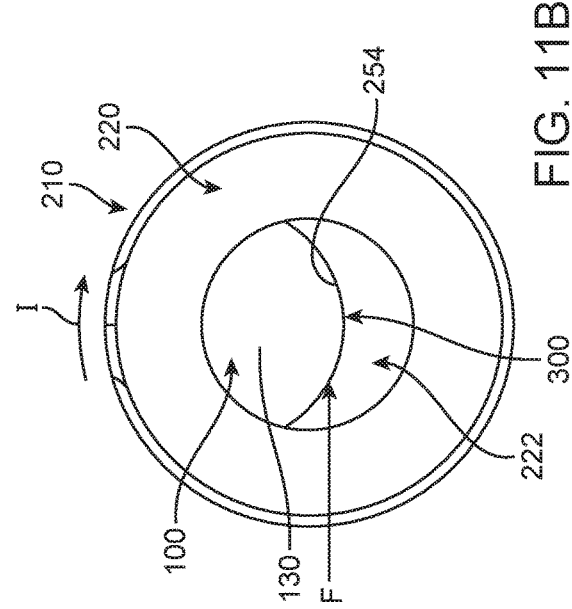

During use, the drive chuck 210 is driven by the motor (not shown) of the powered handpiece 24 (FIG. 1), and caused to rotate about the axis of rotation R. This forced rotation is transferred onto the surgical cutting tool 100 at the interface between the tang 130 and the drive chuck engagement zone 272 (referenced generally). As reflected by the functional diagrams of FIGS. 11A and 11B, the primary central axis A1 of the cutting tool 100 and the major axis M1 of the drive chuck 210 are aligned with the axis of rotation R. The drive axis A2 of the surgical cutting tool 100 and the minor axis M2 of the drive chuck 210 are aligned, and are slanted relative to the axis of rotation R. This off-set arrangement creates a lever arm at the tang 130 and by which the surgical tool 100 is driven. Rotation of the drive chuck 210 about the axis of rotation R (identified by the arrow "I" in FIG. 11B) is applied as a drive force (identified by the arrow "F" in FIG. 11B) on to the tang 130 as a shear force interference. By placing the tang 130 into shear as opposed to pure torsion (as with conventional powered handpiece/rotary surgical cutting tool interfaces), stiffness of the joint between the surgical cutting tool 100 and the drive chuck 210 is enhanced and the level of contact stress being applied is reduced. FIG. 11B indicates at 300 a region of driven interface between the drive chuck 210 (e.g., the engagement surface 254) and the tang 130 and illustrates that possible point loading of the tang 130 does not occur. Further, the relatively large surface area of driven interface minimizes or even eliminates possible backlash between the drive chuck 210 and the tang 130. A crank shaft-like torque transfer effect is generated, whereby the drive force F applied to the slanted axis tang 130 is transmitted as a torque on to a remainder of the surgical cutting tool 100, causing the surgical cutting tool 100 to rotate about the primary central axis A1 (that, again, is aligned with the axis of rotation R).

The drive chuck 210 described above is but one acceptable embodiment envisioned by the present disclosure. The powered handpieces of the present disclosure can incorporate a wide variety of differing drive chuck constructions appropriate for interfacing with the slanted axis tang associated with the particular surgical cutting tool (e.g., one of skill will recognize that a size and shape of any tool-receiving passage provided with the drive chuck will generally coincide with geometries of the surgical cutting tool, such as any of the surgical cutting tools described above). Further, the powered handpieces of the present disclosure optionally include additional components for rotatably supporting the drive chuck and/or facilitating manual release of the surgical cutting tool as will be recognized by those of skill in the art.

Rotary surgical cutting tools, powered handpieces, and resultant surgical cutting systems of the present disclosure provide marked improvements over previous designs. The surgical cutting tools with a slanted axis, tapered cylindrical tang and corresponding powered handpiece drive chuck designs provide superior performance because backlash is minimized or even eliminated. Point loading at the tang/drive chuck interface is decreased (as compared to conventional designs), that in turn improves tool longevity. The surgical cutting tools of the present disclosure are easily inserted by a user. In addition, the surgical cutting tools of the present disclosure represent a cost savings over conventional designs in that the slanted axis drive tang is can be a simple shape that is readily formed or constructed into a conventional, right cylinder tool shaft.

Although the present disclosure has been described with reference to preferred embodiments, workers skilled in the art will recognize that changes can be made in form and detail without departing from the spirit and scope of the present disclosure.

What is claimed is:

1. A surgical cutting tool for use in the dissection of bone, biomaterials, and/or other tissue when mated with a motor, the surgical tool comprising:
   an elongated shaft defining opposing, first and second ends, a dissection portion adjacent the first end, a coupling portion adjacent the second end, and an intermediate portion between the dissection and coupling portions, the intermediate portion defining a primary central axis of the shaft;
   wherein the coupling portion includes a tang having a tapered cylindrical shape that defines a drive axis, the tapered cylindrical shape defining a perimeter shape in a cross-sectional plane perpendicular to the primary central axis having first and second continuously curved segments combining to define at least 80% of a perimeter length of the perimeter shape;
   and further wherein an arc length of the first continuously curved segment differs from an arc length of the second continuously curved segment;
   and even further wherein the perimeter shape of at least one location along the tang consists solely of the first and second continuously curved segments, including the first and second continuously curved segments intersecting one another at opposing lines of intersection;
   and even further wherein the drive axis is slanted with respect to the primary central axis.

2. The surgical cutting tool of claim 1, wherein the tapered cylindrical shape is a non-symmetrical tapered cylindrical shape.

3. The surgical cutting tool of claim 1, wherein the primary central axis and the drive axis form an oblique angle.

4. The surgical cutting tool of claim 1, wherein a slant axis is defined at an intersection of the primary central axis and the drive axis, and further wherein the slant axis is in the range of 3-20 degrees.

5. The surgical cutting tool of claim 1, wherein the drive axis extends through a centroid of a shape of the tang in first and second spaced apart transverse cross-sectional planes, the first and second transverse cross-sectional planes being perpendicular to the primary central axis.

6. The surgical cutting tool of claim 1, wherein the arc lengths of the first and second continuously curved segments decrease in extension toward the second end.

7. The surgical cutting tool of claim 1, wherein the first and second continuously curved segments are convex curves.

8. The surgical cutting tool of claim 1, wherein a shape of the tang includes first and second partial cylinder regions.

9. The surgical cutting tool of claim 1, wherein in the cross-sectional plane perpendicular to the primary central axis, the perimeter shape of the tang is non-flattened.

10. The surgical cutting tool of claim 1, wherein a shape of the tang tapers in maximum outer dimension in extension to the second end.

11. The surgical cutting tool of claim 1, wherein the coupling portion further includes an axial retention feature.

12. The surgical cutting tool of claim 11, wherein the axial retention feature includes a circumferential groove between the tang and the intermediate portion.

13. The surgical cutting tool of claim 11, wherein the axial retention feature includes a slot along the tang.

14. The surgical cutting tool of claim 1, wherein the tang defines a tapering diameter in a direction of the second end and non-symmetric relative to the primary central axis.

15. The surgical cutting tool of claim 1, wherein at least a majority of the intermediate portion is an elongated right cylinder defining the primary central axis.

16. A surgical system for cutting tissue, the system comprising:
   a powered handpiece including:
      a housing,
      a drive shaft rotatably maintained by the housing, a coupling assembly disposed within the housing and including a drive chuck connected to the drive shaft; and a surgical cutting tool releasably connectable to the powered handpiece, the surgical cutting tool including:

an elongated shaft defining opposing, first and second ends, a dissection portion adjacent the first end, a coupling portion adjacent the second end, and an intermediate portion between the dissection and coupling portions, the intermediate portion defining a primary central axis of the shaft;

wherein the coupling portion includes a tang having a tapered cylindrical shape that defines a drive axis, the tapered cylindrical shape defining a perimeter shape in a cross-sectional plane perpendicular to the primary central axis having two continuously curved segments combining to define at least 80% of a perimeter length of the perimeter shape;

and further wherein in the cross-sectional plane perpendicular to the primary central axis, an entirety of the perimeter shape of the tang is non-flattened;

and even further wherein the drive axis is slanted with respect to the primary central axis;

wherein the system is configured such that upon insertion of the tang into the drive chuck and rotation of the drive chuck, a drive force applied to the tang is transmitted as a torque to the intermediate portion about the primary central axis.

17. The surgical system of claim 16, wherein the powered handpiece is configured such that the drive chuck is rotatably driven about an axis of rotation aligned with the primary central axis.

18. The surgical system of claim 17, wherein rotation of the drive chuck imparts a shear force on to the tang.

19. A surgical cutting tool for use in the dissection of bone, biomaterials, and/or other tissue when mated with a motor, the surgical tool comprising:

an elongated shaft defining opposing, first and second ends, a dissection portion adjacent the first end, a coupling portion adjacent the second end, and an intermediate portion between the dissection and coupling portions, the intermediate portion defining a primary central axis of the shaft;

wherein the coupling portion includes a tang having a tapered cylindrical shape that defines a drive axis;

wherein the coupling portion further includes an axial retention feature including a circumferential groove between the tang and the intermediate portion;

and further wherein the drive axis is slanted with respect to the primary central axis.

* * * * *